United States Patent [19]

Huebeck et al.

[11] Patent Number: 4,850,003
[45] Date of Patent: Jul. 18, 1989

[54] APPARATUS FOR POSITIONING A PATIENT'S HEAD FOR PRODUCING REMOTE X-RAY PHOTOGRAPHS

[75] Inventors: Erich Huebeck; Heinrich Schmitt, both of Bensheim; Dieter Molitor, Buerstadt, all of Fed. Rep. of Germany

[73] Assignee: Siemens Aktiengesellschaft, Berlin and Munich, Fed. Rep. of Germany

[21] Appl. No.: 100,222

[22] Filed: Sep. 23, 1987

[30] Foreign Application Priority Data

Sep. 26, 1986 [DE] Fed. Rep. of Germany ....... 3632788

[51] Int. Cl.⁴ ............................................. G03B 42/02
[52] U.S. Cl. .................... 378/179; 378/177; 378/180; 378/38; 378/208
[58] Field of Search .................. 378/38–40, 378/177–180, 208

[56] References Cited

U.S. PATENT DOCUMENTS

| | | |
|---|---|---|
| 2,717,314 | 9/1955 | Delk, Sr. ........................ 378/180 |
| 2,846,587 | 8/1958 | Thurow ......................... 378/180 |
| 2,903,588 | 9/1959 | Minnich ......................... 378/180 |
| 3,536,913 | 10/1970 | Huchel ........................... 378/40 |
| 3,643,095 | 2/1972 | Shuster .......................... 250/105 |
| 3,737,660 | 6/1973 | Ando et al. ..................... 378/39 |
| 3,790,803 | 2/1974 | Phillips ........................... 250/490 |
| 3,936,641 | 2/1976 | Heimar ........................... 378/38 |
| 4,088,893 | 5/1978 | Schroeder ....................... 378/180 |
| 4,232,227 | 11/1980 | Firkenzeller et al. ........... 378/177 |

FOREIGN PATENT DOCUMENTS 2335918 1/1974 Fed. Rep. of Germany.
3221963 12/1983 Fed. Rep. of Germany.

OTHER PUBLICATIONS

Siemens Sale Brochure "Orthoceph 10", pp. 12, 13.

Primary Examiner—Janice A. Howell
Assistant Examiner—John C. Freeman

[57] ABSTRACT

The invention is directed to an apparatus for positioning a patient's head for producing a remote X-ray photograph of the skull of the patient. The apparatus includes a device for holding the skull, which is mounted at one end of a cross carrier which is connected to an X-ray diagnostics installation for producing slice exposures of the jaw of a patient. The skull holder contains ear button holders which are adjustable, as well as a nose support for positioning the patient in the skull holder. The apparatus also includes a device for mounting a film cassette, which device is adjustable in a direction towards the radiation source of the X-ray diagnostics installation. In order to be able to make reproducibile temporomaxillary joint exposures, the skull holder is mounted to pivot around a horizontal axis so that the head of the patient can be adjusted in various inclined positions with relation to the sagittal plane.

12 Claims, 3 Drawing Sheets

APPARATUS FOR POSITIONING A PATIENT'S HEAD FOR PRODUCING REMOTE X-RAY PHOTOGRAPHS

BACKGROUND OF THE INVENTION

The present invention is directed to an apparatus for positioning a patient's head for producing remote X-ray photographs of the skull of a patient, which photographs are referred to as ceph exposures. The apparatus contains a cross carrier member having one end adapted to be connected to an X-ray diagnostics installation for the production of panoramic slice exposures of the jaw of a patient and the other or second end supporting a skull holder which contains a part rotatable around a vertical axis on which two adjustable ear buttons or pins are mounted and also a supporting part for engaging the nasion of the patient, which supporting part is adjustable at least in height and depth. In addition, a film cassette holder is adjustably mounted on the second end of the carrier member and is adjustable in the direction of the carrier member towards the source of radiation of the X-ray diagnostics installation.

An apparatus of this general type is sold under the trade name ORTHOCEPH 10 and includes support means having a part which is rotatable around a vertical axis on which a pair of adjustable ear buttons or pins and an adjustable nose support are provided. Various skull photographs, for example from the front toward the back and vice versa, which are referred to as p.a. and a.p. photographs, respectively, as well as lateral exposures can be easily produced with such an apparatus.

SUMMARY OF THE INVENTION

The object of the present invention is to provide an improved apparatus in which special exposures of the temporomaxillary joints can also be produced in a reproducible fashion in addition to the aforementioned skull photographs. Such special temporomaxillary joint exposures require a precise positioning of the condyle with respect to the X-ray to be made and correspondingly require adjustment of the position of the patient's head. Two exposures are usually required for the identification of the precise position of the condyles and includes what is referred to as a submento-vertical exposure with which the other condyle axis angle can be identified and a second exposure which is referred to as an a.p. exposure with which the intersecting angle of the condyle axis can be identified in a sagittal direction.

To accomplish these goals, the present invention is directed to an improvement in an apparatus for positioning a patient's head for producing remote X-ray photographs of the skull of a patient, said apparatus including a cross or carrier member having a first end adapted for connection to a dental X-ray diagnostics apparatus, which produces slice exposures of the jaw of a patient, and a second or other end of the carrier member supports first means including a support means for holding a skull, including a part rotatable around a vertical axis, two ear pins lying diametrically opposite one another and being adjustably mounted on said rotatable part, a seating part adjustable at least in height and depth for forming a nose support of the patient being arranged on said rotatable part, said first means including means supporting a film cassette which is adjustable in a direction along the axis extending toward the source of radiation of the X-ray diagnostics installation. The improvements are mounting means for pivotally mounting the support means for rotating around a horizontal axis on the second end of the carrier member so that the patient's head is adjustable into various inclined positions with reference to the sagittal plane and the patient's head is positionable by the rotatable part of the support means around a vertical axis so that the temporomaxillary joints can be imaged in two planes, respectively, perpendicular to the condyle axis.

A significant advantage of the apparatus of the present invention is that it is adaptable to a panorama X-ray apparatus and, thus, slice and static photographs, particularly pertaining to the temporomaxillary joints can be produced by one apparatus. The existing degree of freedom allows the positioning of the patient's head for exposure in two planes residing perpendicular relative to one another, namely both in the transmaxillary direction, for example perpendicular to the condyle axis, as well as in the transcranial direction, for example parallel to the condyle axis or, respectively, along the temporomaxillary joint gap.

To accomplish these exposures, it is required that the skull-holding means can be pivoted around a horizontal axis, wherein the ear pin or button holders and the nasion support element exactly fit the patient's head for reproducible exposures. By tilting and turning, the patient's head can be positioned so that the initially cited standard exposures, as well as special temporomaxillary joint exposures can be produced in a simple way with the same apparatus.

Such a special temporomaxillary joint exposure can be achieved with another known apparatus, which is disclosed in U.S. Pat. No. 3,875,412, whose disclosure is incorporated by reference thereto and which corresponds to German Pat. No. 23 35 918. However, the apparatus of this patent is not suitable for being adapted to an X-ray diagnostics apparatus for the production of paroramic slice exposures, and this apparatus, on the contrary, represents an independent X-ray apparatus in which the patient's head, which is fixed only by the ear pin mounts, can be tilted on the axis of the ear pin mounts so that a particularly non-reproducible temporomaxillary joint exposure can be produced despite the many possibilities of adjustments cited therein. Moreover, the adjustment mechanism set forth therein, particularly the double carriage arrangement for the head holders, are comparatively involved.

In comparison thereto, the apparatus of the present invention represents a solution which is significantly simpler in structural terms. The carrying rod accepting the skull-holding means is advantageously height-adjustable, which opens up the possibility of being able to also register the last cervical vertebra on the film without a change of format. The telescoping tubes are preferably provided for the height adjustment, and this is expediently cladded by an accordion bellows. The carrying tube is advantageously adjustably held on a housing which is secured to the carrier member, and this housing simultaneously contains guide bushings for the acceptance of guide elements for the film cassette holder.

Other advantages and developments and improvements will be readily apparent from the following description of the preferred embodiments, drawings and claims.

DESCRIPTION OF THE PREFERRED EMBODIMENTS

Figure 1:
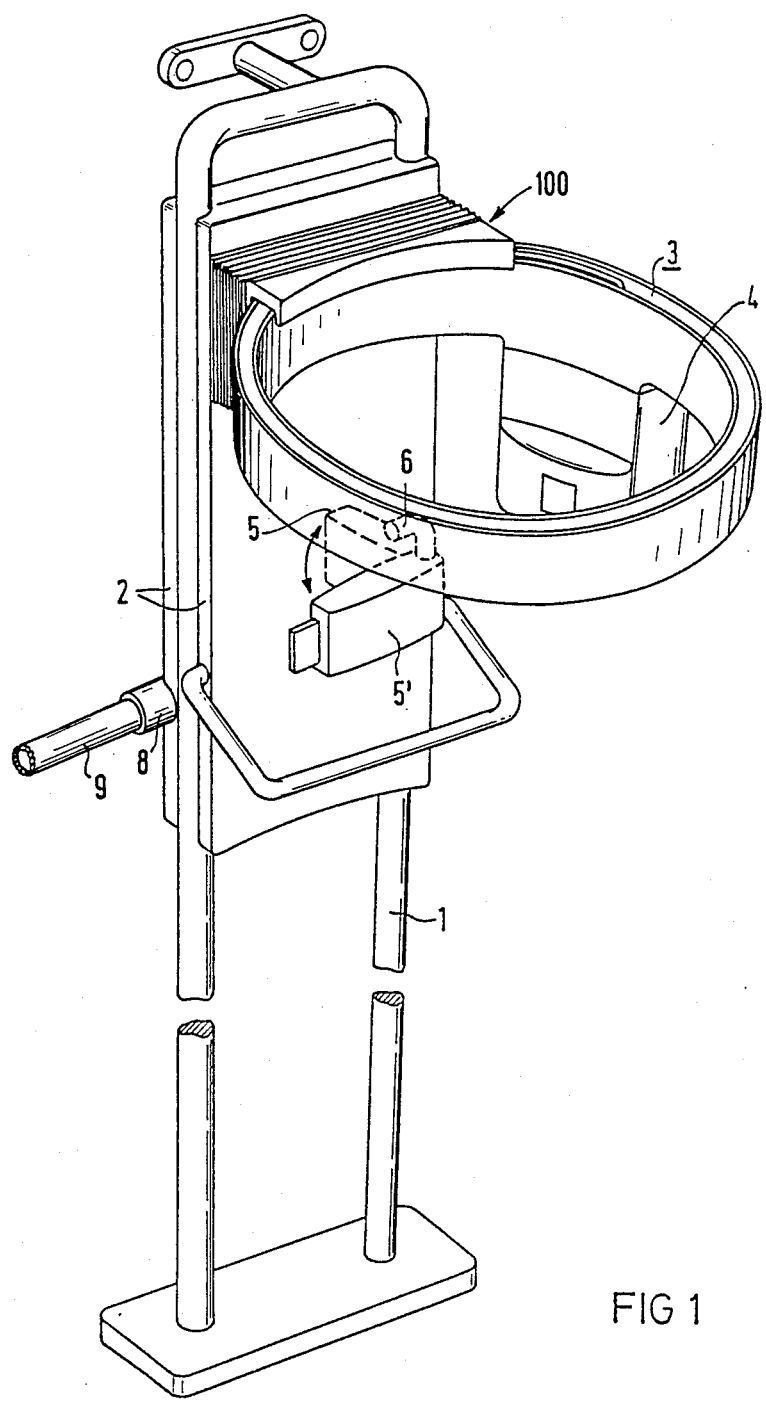
FIG. 1 is a perspective view of a dental X-ray diagnostics apparatus for producing panoramic slice exposures of a jaw of a patient.

A dental X-ray diagnostics apparatus is generally indicated at 100 in FIG. 1, and is for producing panoramic slice exposures of a patient. The apparatus 100 contains a stand 1, which is formed of two upright pipes, which support a carriage 2 that is height-adjustable on the stand 1. A rotational unit, in the form of a closed ring 3, is mounted on the carriage 2, and this rotational unit, in turn, contains an x-radiator 4 and, diametrically opposite thereto, a film cassette holder 5 for panoramic slice exposures. Whereas the x-radiator 4 is rigidly mounted on the ring 4, the film cassette holder 5 is held for pivotal movement around an angled carrier arm 6. The film cassette holder 5 can, thus, be brought from a position shown in broken lines which is suitable for a normal slice exposure into a non-used position 5', shown in solid lines. In this non-use position 5', the X-ray apparatus 100, together with an apparatus 101 of FIGS. 2-5, is suitable for what is referred to as ceph exposures, which are for producing remote photographs of the skull of a patient. In order to be able to make such a remote photograph, a head and cassette holder, shown in FIG. 2, must be held at a defined distance of about 1 to 2 meters from the source of radiation of the x-radiator 4. For this purpose, an adaptor 8 is provided on a side of the carriage 2 and the head positioning cassette holder apparatus set forth hereinlater is adapted to be mounted on a cross or carrier member 9 who has one or a first end secured in the adaptor 8.

The principals of the present invention are particularly useful in the apparatus or first means 101, which has support or position means for supporting or holding the skull or the head of the patient in a given position and also includes holder means for supporting a film cassette 18.

Figure 2:
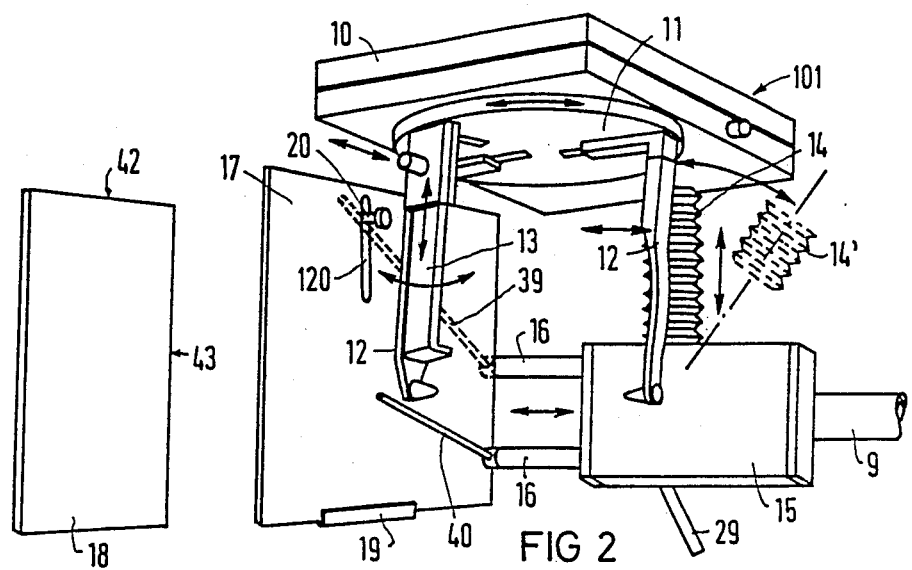
FIG. 2 is a perspective view of an embodiment of the inventive apparatus in accordance with the present invention for attachment to the device of FIG. 1.

As illustrated in FIG. 2, the support means 10 has a rotational part 11, which is held in a known fashion for rotation around a vertical axis. The dish or part 11 adjustably supports two ear button holders or pins 12, which slide diametrically opposite one another and the part 11 also supports a nasion support part 13, which, with the ear pins 12, forms a roughly triangular arrangement in the plan view. The nasion support part 13 is held on the rotating dish by adjustable means which allows adjustment for both height and depth, as indicated by the arrow directions, as well as to swivel around a journal bearing.

The skull-holding or support means is connected to the cross member or carrier member 9 by mounting means which includes a vertically extending carrier part 14, which is mounted for rotation on a housing 15, which is mounted on the second or outer end of the carrier member 9. The housing 15 supports two horizontal carrying rods 16 for a film cassette holder 17. The two carrying rods 16, which form a first carrier part, are held in the housing adjustable, as indicated by the double arrow.

The film cassette 18, which contains the X-ray film, is introduced into the film cassette holder 17 to stand in a vertical plane. To guide the cassette, the holder 17 has guide elements 19 and 20.

Figure 3:
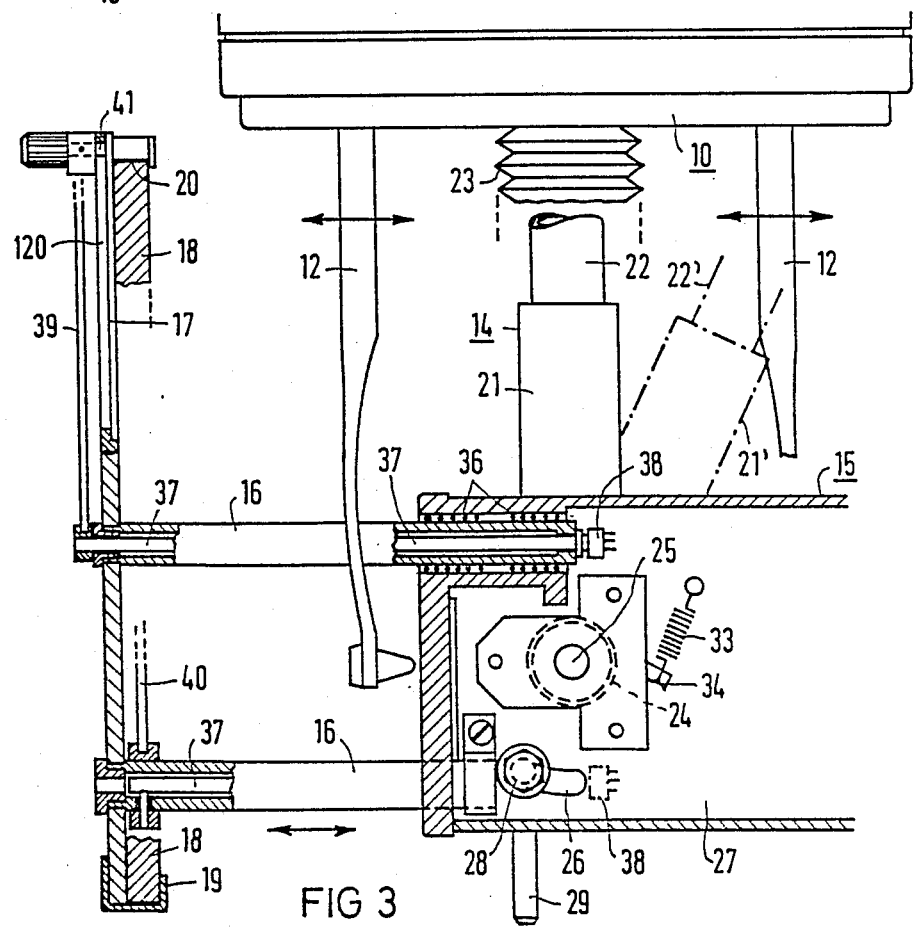
FIG. 3 is a partial cross sectional view, with portions in elevation, of the device of FIG. 2.

As best illustrated in FIG. 3, the carrier part or column 14 is composed of two pipes 21 and 22, which are telescoped into one another and are covered by a shared bellows 23. In order to achieve different extended lengths and, thus, a height adjustment for the skull holder means relative to the housing 15, one of the two pipes is provided with a longitudinal channel and the other is provided with a bore, through which a set screw 24 (FIG. 5) is engaged. In addition to the height adjustability which the particular serves a purpose for coimaging the last cervical vertebra in special exposures, the overall skull-holding means is also pivotable around a horizontal axis 25 formed by a journal bearing or bearing means, illustrated in FIGS. 3 and 4. The pivoting can be between the vertical position in bold line of FIGS. 2 and 3 to the broken line position 14' of FIG. 2 or the chain-line position 21', 22' of FIG. 3. The angle of inclination or pivoting on the axis 25 is limited by a threaded pin 28 extending through an annular slot 26 (FIG. 3) in a housing wall 27. The pin 28, as best illustrated in FIG. 5, also extends through a lower end of the tube 21 and is provided with a clamping lever 29, which is also threaded onto the pin 28 between the pipe 21 and the housing 15 so that the parts are locked together when the lever is actuated.

Figure 4:
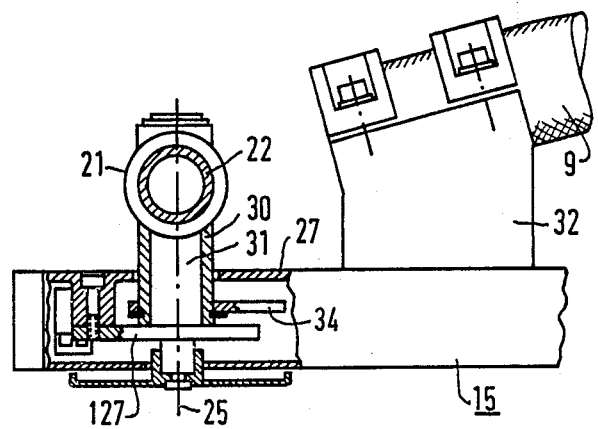
FIG. 4 is a top view, with portions broken away for purposes of elevation, of the support for the head-holding means of FIG. 2.
Figure 5:
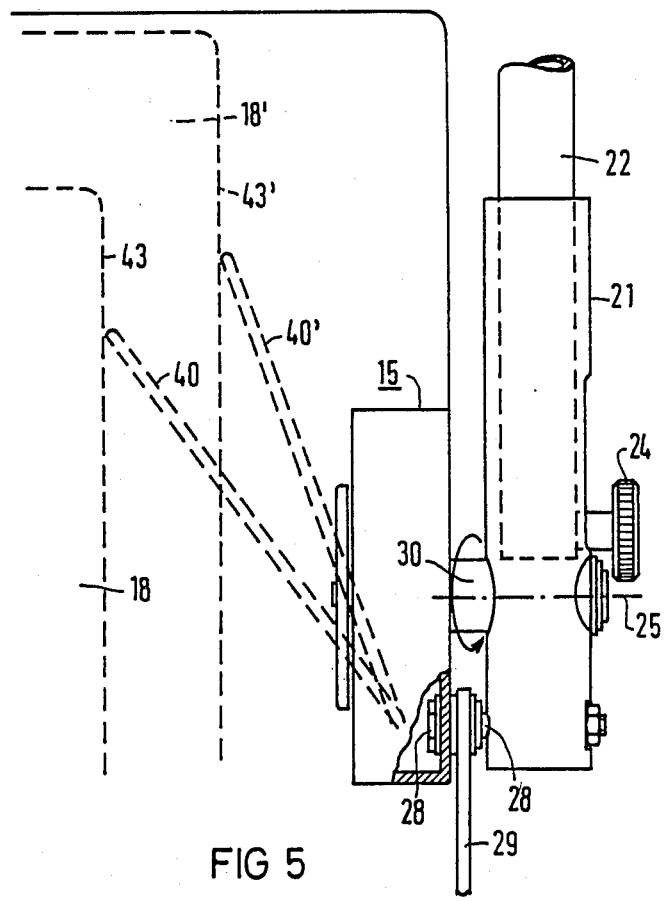
FIG. 5 is an end view of the device of the support means of FIG. 2 with portions broken away for purposes of illustration.

As may be seen in FIG. 4 of the housing 15, the supporting part pivots on the housing by bushing or sleeve member 30 which penetrates the lower telescopic pipe 21 transverse relative to the longitudinal axis and which is rigidly connected thereto. The member 30 is received on a bearing neck or axle 31, which neck is secured to the housing member 127. The bushing 30 can turn on the axle 31. The carrier member 9 is secured by a shoulder 32 of the housing 15 with its longitudinal axis extending at a relatively small, acute angle relative to the plane of the housing wall 27.

In order for the skull holder means to retain its basic position when the clamping lever 29 is released, a tension spring 33 (FIG. 3) is provided in the housing 15. The spring 33 is connected to a wall of the housing and has the other end connected to a supporting part 34 which is secured to the bushing 30 at a fixed angle and forms a lever arm relative to the rotational axis 25.

The two supporting rods 16 are fashioned as pipes and are guided in linear bearings such as 36 in an easy-running fashion. A transmission element 37, which is either a rod or sleeve and is mounted within each of the tubular rods 16 and has one end of these elements being connected at a fixed angle with an angle generator in the form of a potentiometer 38. The other end is connected at a fixed angle with a sensing lever 39 or 40. The sensing lever 39 is arranged following the film cassette holder 17 and the sensing lever 40 is arranged preceding or in front of the film cassette holder 17. The two sensing levers are part of a detecting arrangement, which will provide the film cassette format in an automatically identifiable fashion when the cassette is slipped into the film cassette holder 17. Under given conditions, the identification will be displayed on a display and the signals are used to insure that the primary diaphragm, which belongs to a selected film format, is automatically brought into the beam path between the radiation source and the subject.

As illustrated in FIG. 3, the sensing lever 39 is connected, first, to a transmission rod 37, which extends through the film cassette holder 17 and is connected with an additional cross member 41, which extends back through a slot 120 in the film cassette holder 17 and contains a guide element 20 acting as a sensing head. The cross member 41 can move along the lever 39 as it moves in the slot 120. The element 20 will ride on the reference surface 42 which defines an upper edge of the film cassette format 18. The free end of the sensing lever 40 will bear against a reference surface 43, which corresponds to the width of the selected film cassette format, as illustrated in FIGS. 2 and 5. For example, with a cassette 18, the lever 40 assumes one position in FIG. 5. However, with cassette 18' with edge 43', the lever is in position 40'. The respective pivoting angle of the two sensing levers 39 and 40 correspond to the engagement of their ends against the reference surfaces 42 and 43, respectively, of the emplaced film cassette and identifies the selected film cassette format.

Given a corresponding processing of the signals acquired from the angle generators 38, an indication can also be made that a film cassette 18 is inserted in the holder 17.

Although various minor modifications may be suggested by those versed in the art, it should be understood that we wish to embody within the scope of the patent granted hereon all such modifications as reasonably and properly come within the scope of our contribution to the art.

We claim:

1. In an apparatus for positioning a patient's head for producing remote X-ray photographs of the skull of the patient, said apparatus including a carrier member having a first end and a second end; said first end forming a connection to a dental X-ray diagnostics apparatus which has a radiation source providing a beam of X-ray radiation and produces slice exposures of the jaw of a patient; said second end supporting position means for holding a skull and holder means for supporting a film cassette; said position means containing a part rotatable around a vertical axis, two ear button holders being adjustably mounted on said rotatable part to lie diametrically opposite one another relative to said vertical axis, and a nasion support being adjustably mounted for height and depth on said rotatable part for engaging a nasion of the patient; said holder means being adjustable along a direction of the beam of radiation from said radiation source to change a spacing of said film cassette from said radiation source, the improvements comprising a housing being secured to the second end of said carrier member, said housing supporting a first carrier part for said holder means and a vertically extending second carrier part for the position means, said second carrier part having an upper end fixedly mounted with the supporting part and a lower end having pivotal means for mounting the second carrier part in the housing for pivotal movement around a horizontal axis so that the patient's head is adjustable into various inclined positions with reference to the sagittal plane and the patient is positionable via said rotatable part around said vertical axis so that the temporomaxillary joints can be imaged in two planes, respectively, perpendicular to the condyle axis.

2. In an apparatus according to claim 1, wherein the upper end of the second carrier part is height adjustable with respect to said housing so that a spacing of the position means for holding the skull can be adjusted relative to the housing.

3. In an apparatus according to claim 2, wherein the second carrier part is composed of telescoping tubes which have means for fixing them in various axial positions relative to one another.

4. In an apparatus according to claim 3, wherein the telescoping tubes are covered by an accordion bellows.

5. In an apparatus according to claim 1, wherein the pivotal means includes bearing means being mounted for movement in the housing around said horizontal axis.

6. In an apparatus according to claim 5, wherein the bearing means includes a sleeve member extending through the walls of the housing and being rotatable on an axle carried by said housing.

7. In an apparatus according to claim 6, wherein a lever arm is secured to said sleeve member, said lever arm being connected to the housing by a spring element for the purpose of stabilizing said position means in a basic position.

8. In an apparatus according to claim 5, which includes means for locking the second carrier part in relatively inclined positions to said housing.

9. In an apparatus according to claim 8, wherein the means for locking includes a threaded rod extending through a slot in a wall of the housing and a portion of the second carrier part, said threaded rod containing a clamp lever screwed to said threaded rod, said rod coacting with the slot in the wall of the housing to limit inclination of said position means.

10. In an apparatus according to claim 5, wherein the first carrier part supporting the holder means is composed of a pair of carrying rods received in horizontally extending bearings in said housing so that the film cassette holder can be moved in a horizontal direction relative to said vertical axis.

11. In an apparatus according to claim 10, wherein the carrying rods are hollow tubes each having a transmission element extending therethrough, each of said transmission elements having one end being connected to a corresponding angle generator in said housing and having an opposite end of each transmission element secured to a corresponding lever arm for engaging sides of the film cassette so that angular displacement of each of said corresponding lever arm will occur with the insertion of the film cassette on said holder with each of said angle generators creating an electrical signal, which is dependent on the amount of angular displacement of said corresponding lever arm.

12. In an apparatus according to claim 1, wherein said horizontal axis of the pivotal means extends substantailly at right angles to the direction of the beam of X-ray radiation.

* * * * *